US009113929B2

(12) United States Patent
Parsonage

(10) Patent No.: US 9,113,929 B2
(45) Date of Patent: Aug. 25, 2015

(54) NON-ELECTRIC FIELD RENAL DENERVATION ELECTRODE

(71) Applicant: St. Jude Medical, Cardiology Division, Inc., St. Paul, MN (US)

(72) Inventor: Edward E. Parsonage, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 102 days.

(21) Appl. No.: 13/781,136

(22) Filed: Feb. 28, 2013

(65) Prior Publication Data

US 2013/0282000 A1    Oct. 24, 2013

Related U.S. Application Data

(60) Provisional application No. 61/635,512, filed on Apr. 19, 2012.

(51) Int. Cl.
*A61B 18/04* (2006.01)
*A61B 18/18* (2006.01)
*A61B 18/14* (2006.01)
(Continued)

(52) U.S. Cl.
CPC ............ *A61B 18/18* (2013.01); *A61B 18/1492* (2013.01); *A61B 18/082* (2013.01); *A61B 2018/0016* (2013.01); *A61B 2018/00059* (2013.01); *A61B 2018/00083* (2013.01); *A61B 2018/00095* (2013.01); *A61B 2018/00136* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01)

(58) Field of Classification Search
None
See application file for complete search history.

(56) References Cited

U.S. PATENT DOCUMENTS 3,650,277 A    3/1972    Sjostrand et al.
4,658,819 A    4/1987    Harris et al.
(Continued)

FOREIGN PATENT DOCUMENTS

WO    97/45157    12/1997
WO    00/66020    11/2000
(Continued)

OTHER PUBLICATIONS

Abboud, Francois M., The Sympathetic System in Hypertension, State-of-the-Art Review, Hypertension Journal of the American Heart Association, Hypertension 4 (suppl II): II-208-II-225, 1982.
(Continued)

*Primary Examiner* — Brian T Gedeon
(74) *Attorney, Agent, or Firm* — Armstrong Teasdale LLP

(57) ABSTRACT

A renal denervation device can include an elongated catheter body extending along a longitudinal axis, and an assembly connected to the catheter body. The assembly includes a plurality of heating elements connected to the catheter body. Each heating element has a conductor and a layer of an RF dissipating material such as a polymer overlying the conductor. During operation of the device, the layer of RF dissipating material is disposed between the conductor and body tissues of a subject. The layer of RF dissipating material is substantially thicker than the Debye length within the material in order to reduce the electric field reaching the tissue and to eliminate direct contact of the electrode with the body tissue.

22 Claims, 3 Drawing Sheets

(51) Int. Cl.
*A61B 18/08* (2006.01)
*A61B 18/00* (2006.01)

(56) References Cited

U.S. PATENT DOCUMENTS

| | | | |
|---|---|---|---|
| 5,035,694 | A | 7/1991 | Kasprzyk et al. |
| 5,255,679 | A | 10/1993 | Imran |
| 5,300,068 | A | 4/1994 | Rosar et al. |
| 5,368,591 | A | 11/1994 | Lennox et al. |
| 5,387,233 | A | 2/1995 | Alferness et al. |
| 5,465,717 | A | 11/1995 | Imran et al. |
| 5,531,779 | A | 7/1996 | Dahl et al. |
| 5,598,848 | A | 2/1997 | Swanson et al. |
| 5,607,462 | A | 3/1997 | Imran |
| 5,628,313 | A | 5/1997 | Webster, Jr. |
| 5,676,662 | A | 10/1997 | Fleischhacker et al. |
| 5,707,400 | A | 1/1998 | Terry, Jr. et al. |
| 5,769,077 | A | 6/1998 | Lindegren |
| 5,772,590 | A | 6/1998 | Webster, Jr. |
| 5,893,885 | A | 4/1999 | Webster, Jr. |
| 5,897,553 | A | 4/1999 | Mulier et al. |
| 5,954,649 | A | 9/1999 | Chia et al. |
| 5,954,719 | A | 9/1999 | Chen et al. |
| 5,954,742 | A | 9/1999 | Osypka |
| 6,004,269 | A | 12/1999 | Crowley et al. |
| 6,012,457 | A | 1/2000 | Lesh |
| 6,016,437 | A | 1/2000 | Tu et al. |
| 6,024,740 | A | 2/2000 | Lesh et al. |
| 6,073,048 | A | 6/2000 | Kieval et al. |
| 6,096,037 | A | 8/2000 | Mulier et al. |
| 6,117,101 | A | 9/2000 | Diederich et al. |
| 6,161,543 | A | 12/2000 | Cox et al. |
| 6,178,349 | B1 | 1/2001 | Kieval |
| 6,200,312 | B1 | 3/2001 | Zikorus et al. |
| 6,216,044 | B1 | 4/2001 | Kordis |
| 6,233,491 | B1 | 5/2001 | Kordis et al. |
| 6,283,951 | B1 | 9/2001 | Flaherty et al. |
| 6,287,608 | B1 | 9/2001 | Levin et al. |
| 6,292,695 | B1 | 9/2001 | Webster, Jr. et al. |
| 6,322,559 | B1 | 11/2001 | Daulton et al. |
| 6,460,545 | B2 | 10/2002 | Kordis |
| 6,522,926 | B1 | 2/2003 | Kieval et al. |
| 6,613,045 | B1 | 9/2003 | Laufer et al. |
| 6,616,624 | B1 | 9/2003 | Kieval |
| 6,635,054 | B2 | 10/2003 | Fjield et al. |
| 6,656,174 | B1 | 12/2003 | Hegde et al. |
| 6,669,655 | B1 | 12/2003 | Acker et al. |
| 6,699,231 | B1 | 3/2004 | Sterman et al. |
| 6,748,255 | B2 | 6/2004 | Fuimaono et al. |
| 6,805,131 | B2 | 10/2004 | Kordis |
| 6,845,267 | B2 | 1/2005 | Harrison et al. |
| 6,954,977 | B2 | 10/2005 | Maguire et al. |
| 6,970,730 | B2 | 11/2005 | Fuimaono et al. |
| 6,978,174 | B2 | 12/2005 | Gelfand et al. |
| 7,122,031 | B2 | 10/2006 | Edwards et al. |
| 7,149,574 | B2 | 12/2006 | Yun et al. |
| 7,155,284 | B1 | 12/2006 | Whitehurst et al. |
| 7,162,303 | B2 | 1/2007 | Levin et al. |
| 7,245,955 | B2 | 7/2007 | Rashidi |
| 7,291,146 | B2 | 11/2007 | Steinke et al. |
| 7,363,076 | B2 | 4/2008 | Yun et al. |
| 7,419,486 | B2 | 9/2008 | Kampa |
| 7,465,288 | B2 | 12/2008 | Dudney et al. |
| 7,468,062 | B2 | 12/2008 | Oral et al. |
| 7,481,803 | B2 | 1/2009 | Kesten et al. |
| 7,617,005 | B2 | 11/2009 | Demarais et al. |
| 7,620,451 | B2 | 11/2009 | Demarais et al. |
| 7,647,115 | B2 | 1/2010 | Levin et al. |
| 7,653,438 | B2 | 1/2010 | Deem et al. |
| 7,717,948 | B2 | 5/2010 | Demarais et al. |
| 7,742,795 | B2 | 6/2010 | Stone et al. |
| 7,756,583 | B2 | 7/2010 | Demarais et al. |
| 7,850,685 | B2 | 12/2010 | Kunis et al. |
| 7,853,333 | B2 | 12/2010 | Demarais |
| 7,873,417 | B2 | 1/2011 | Demarais et al. |
| 7,937,143 | B2 | 5/2011 | Demarais et al. |
| 7,949,407 | B2 | 5/2011 | Kaplan et al. |
| 8,131,371 | B2 | 3/2012 | Demarals et al. |
| 8,131,372 | B2 | 3/2012 | Levin et al. |
| 8,145,316 | B2 | 3/2012 | Deem et al. |
| 8,145,317 | B2 | 3/2012 | Demarais et al. |
| 8,150,518 | B2 | 4/2012 | Levin et al. |
| 8,150,519 | B2 | 4/2012 | Demarais et al. |
| 8,150,520 | B2 | 4/2012 | Demarais et al. |
| 8,175,711 | B2 | 5/2012 | Demarais et al. |
| 8,224,416 | B2 | 7/2012 | de La Rama et al. |
| 8,343,213 | B2 | 1/2013 | Salahieh et al. |
| 8,347,891 | B2 | 1/2013 | Demarais et al. |
| 8,433,423 | B2 | 4/2013 | Demarais |
| 8,442,639 | B2 | 5/2013 | Walker et al. |
| 8,444,640 | B2 | 5/2013 | Demarais et al. |
| 8,454,594 | B2 | 6/2013 | Demarais et al. |
| 8,545,495 | B2 | 10/2013 | Scheib |
| 2002/0068885 | A1 | 6/2002 | Harhen et al. |
| 2002/0120304 | A1 | 8/2002 | Mest |
| 2003/0050681 | A1 | 3/2003 | Pianca et al. |
| 2003/0060858 | A1 | 3/2003 | Kieval et al. |
| 2003/0074039 | A1 | 4/2003 | Puskas |
| 2003/0114739 | A1 | 6/2003 | Fuimaono et al. |
| 2003/0139741 | A1* | 7/2003 | Goble et al. .......... 606/48 |
| 2003/0216792 | A1 | 11/2003 | Levin et al. |
| 2003/0233099 | A1 | 12/2003 | Danaek et al. |
| 2004/0215186 | A1 | 10/2004 | Cornelius et al. |
| 2005/0288730 | A1 | 12/2005 | Deem et al. |
| 2006/0089678 | A1 | 4/2006 | Shalev |
| 2007/0135875 | A1 | 6/2007 | Demarais et al. |
| 2008/0255478 | A1 | 10/2008 | Burdette |
| 2009/0076409 | A1 | 3/2009 | Wu et al. |
| 2010/0016762 | A1 | 1/2010 | Thapliyal et al. |
| 2010/0094209 | A1 | 4/2010 | Drasler et al. |
| 2010/0168737 | A1 | 7/2010 | Grunewald |
| 2010/0249773 | A1 | 9/2010 | Clark et al. |
| 2010/0268307 | A1 | 10/2010 | Demarais et al. |
| 2010/0286684 | A1 | 11/2010 | Hata et al. |
| 2011/0004087 | A1 | 1/2011 | Fish et al. |
| 2011/0118726 | A1 | 5/2011 | De La Rama et al. |
| 2011/0137298 | A1 | 6/2011 | Nguyen et al. |
| 2011/0160720 | A1 | 6/2011 | Johnson |
| 2011/0213231 | A1 | 9/2011 | Hall et al. |
| 2011/0257641 | A1 | 10/2011 | Hastings et al. |
| 2011/0264011 | A1 | 10/2011 | Wu et al. |
| 2011/0264086 | A1 | 10/2011 | Ingle |
| 2012/0143097 | A1 | 6/2012 | Pike, Jr. |
| 2012/0143298 | A1 | 6/2012 | Just et al. |
| 2012/0296232 | A1 | 11/2012 | Ng |
| 2012/0323233 | A1 | 12/2012 | Maguire et al. |
| 2013/0116737 | A1 | 5/2013 | Edwards et al. |
| 2013/0131743 | A1 | 5/2013 | Yamasaki et al. |
| 2013/0144251 | A1 | 6/2013 | Sobotka |
| 2013/0172715 | A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

(56) References Cited

OTHER PUBLICATIONS

Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. 2013 Nov;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters 1987 Feb 10;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, America! Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.

(56) References Cited

OTHER PUBLICATIONS

Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:5259 (2003).
Naidoo, N. et al, Thoracic Splanchnic Nerves: Implications for Splanchnic Denervation, Journal of Anatomy, 2001 Nov;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998.;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, Pace, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, Pace, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, Time Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14 (4):443-458.
Page, Irvine H., The Effect of Renal Efficiency of Lowering Arterial Blood Pressure in Cases of Essential Hypertension and Nephritis, Journal of Clinical Investigation, Nov 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of the American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.

(56) References Cited

OTHER PUBLICATIONS

Poutasse, Eugene F., Surgical Treatment of Renal Hypertension, American Journal of Surgery, vol. 107, Jan. 1964, 97-103.
Pugsley, M.K. et al, The Vascular System An Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol 2013 Apr. 26; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. And Exper.—Theory and Practice, Ag(Suppl.I), 47-57 (1987).

(56) References Cited

OTHER PUBLICATIONS

Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pp.; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. 2002 Mar;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. 1974 Feb 2;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of the American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, the Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.

(56) References Cited

OTHER PUBLICATIONS

Howard, James P. et al, Size of Blood Pressure Reduction from Renal Denervation: Insights from Meta-Analysis of Antihypertensive Drug Trials of 4121 Patients with Focus on Trial Design: The Converge Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoe K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of The American Heart Association, 1998;32:249-254.

Humpreys, Michael H., Renal Nerves and CKD: Is Renal Denervation the Answer?, Journal of The American Socity of Nephrology, 2012, 23: 1-3.

International Search Report and Written Opinion for Application No. PCT/US2010/054637, mailed Jan. 3, 2011.

International Search Report and Written Opinion for Application No. PCT/US2010/054684, mailed Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd24449); Print Issue Date: Sep. 2012. URL: http://onlinelibrary.wiley.com/doi/10.10021ccd.24449/abstract.

Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.

Jais, Pierre et al, Efficacy and Safety of Septal and Left-Atrial Linear Ablation for Atrial Fibrillation, The American Journal of Cardiology, vol. 84 (9A), Nov. 1999, 139R-146R.

Janssen, Ben J.A. et al, Frequency-Dependent Modulation of Renal Blood Flow by Renal Nerve Activity in Conscious Rabbits, American Journal of Physiology, 1997, 273:R597-R608.

Janssen, Ben J.A. et al, Renal Nerves in Hypertension, Miner Electrolyte Metab 1989;15:74-82.

Jin, Yu et al, No Support for Renal Denervation in a Meta-Analysis, JACC vol. 62, No. 21, 2013 Correspondence Nov. 19/26, 2013:2029-30.

Kaltenbach, Benjamin et al, Renal Artery Stenosis After Renal Sympathetic Denervation, J Am Coll Cardiol. Dec. 25, 2012;60(25):2694-5.

Kaltenbach, Benjamin et al, Renal Sympathetic Denervation as Second-Line Therapy in Mild Resistant Hypertension: A Pilot Study, Catheterization and Cardiovascular Interventions 81:335-339 (2013).

Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.

Kandzari, David E. et al, Catheter-Based Renal Denervation for Resistant Hypertension: Rationale and Design of the Symplicity HTN-3 Trial, Clin. Cardiol. 35, 9, 528-535 (2012).

Kapural, Leonardo et al, Radiofrequency Ablation for Chronic Pain Control, Current Pain and Headache Reports 2001, 5:517-525.

Kassab, Salah et al, Renal Denervation Attenuates the Sodium Retention and Hypertension Associated with Obesity, Hypertension vol. 25, No. 4, Part 2 Apr. 1995.

Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.

Katholi, Richard E. et al, Role of the Renal Nerves in the Pathogenesis of One-Kidney Renal Hypertension in the Rat, Hypertension. 1981;3:404-409.

Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243248.

Katritsis, Demosthenes et al, Recurrence of Left Atrium-Pulmonary Vein Conduction Following Successful Disconnection in Asymptomatic Patients, Europace (2004) 6, 425e432.

Killip III, Thomas, Oscillation of Blood Flow and Vascular Resistance During Mayer Waves, Circulation Research, vol. XI, Dec. 1962, 987-993.

Kingwell, Bronwyn A. et al, Assessment of Gain of Tachycardia and Bradycardia Responses of Cardiac Baroreflex, Am J Physiol Heart Circ Physiol 260:H1254-H1263, 1991.

Kirchheim, H. et al, Sympathetic Modulation of Renal Hemodynamics, Renin Release and Sodium Excretion, Klin Wochenschr (1989) 67: 858-864.

Klein, Ge et al, Endovascular Treatment of Renal Artery Aneurysms with Conventional Non-Detachable Microcoils and Guglielmi Detachable Coils, Br J Urol. Jun. 1997; 79(6):852-860.

Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.

Koepke, John P. et al, Functions of the Renal Nerves, The Physiologist, vol. 28, No. 1, Feb. 1985, 47-52.

Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.

Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.

Krum, Henry et al, Device-Based Antihypertensive Therapy: Therapeutic Modulation of the Autonomic Nervous System, Circulation. 2011;123:209-215.

La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.

Labeit, Alexander Michael et al, Changes in the Prevalence, Treatment and Control of Hypertension in Germany? A Clinical-Epidemiological Study of 50.000 Primary Care Patients, Plos One, Dec. 2012, vol. 7, Issue 12, e52229, 1-11.

Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, a.W.D., Hypertension—Treated and Untreated, British Medical Journal, May 1959, 1361-1368.

(56) References Cited

OTHER PUBLICATIONS

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After Symplicity HTN-3: Confused at the Higher Level?; European Heart Journal, doi:10.1093/eurheartyehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/Jun.), 1999: pp. 481-498.

Mahfoud, Felix et al, Expert Consensus Document from the European Society of Cardiology on Catheter-Based Renal Denervation, European Heart Journal, Jul. 2013;34(28):2149-57.

Mancia, Giuseppe et al, Sympathetic Activation in the Pathogenesis of Hypertension and Progression of Organ Damage, Hypertension Journal of The American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com,.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter -based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal But Not Cardiac Sympathetic Activity in Humans; Hypertension Journal of The American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

Millard, F.C. et al, Renal Embolization for Ablation of Function in Renal Failure and Hypertension, Postgraduate Medical Journal (1989) 65, 729-734.

Zazgornik, Jan et al, Bilateral Nephrectomy: The Best, but Often Overlooked, Treatment for Refractory Hypertension in Hemodialysis Patients, AJH 1998; 11:1364-1370.

\* cited by examiner

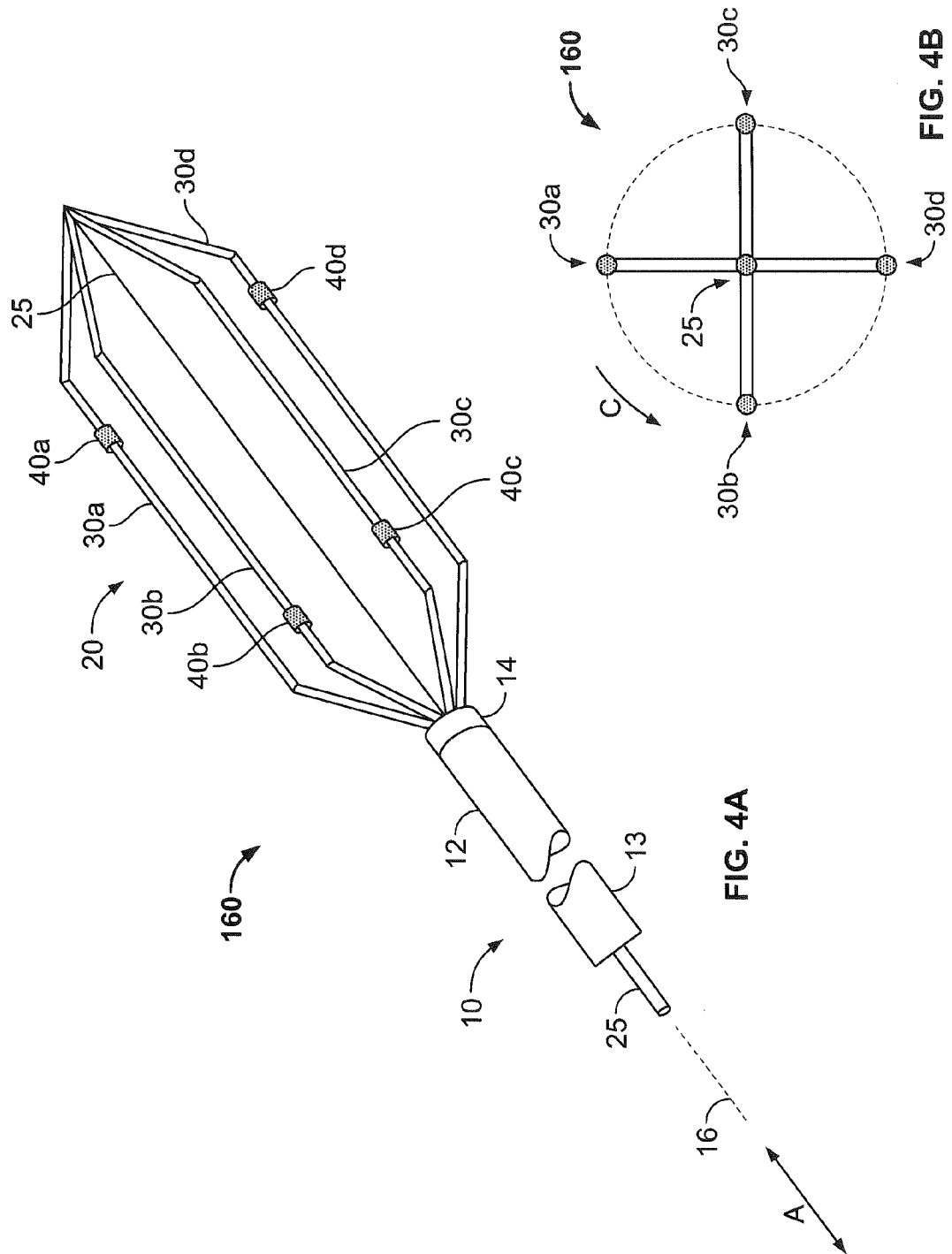

NON-ELECTRIC FIELD RENAL DENERVATION ELECTRODE

CROSS REFERENCE TO RELATED APPLICATION

This application claims the benefit of the filing date of U.S. Provisional Patent Application No. 61/635,512 filed Apr. 19, 2012, the disclosure of which is hereby incorporated herein by reference.

FIELD OF THE INVENTION

This invention relates generally to electrodes for RF energy application and to devices and methods incorporating such electrodes including renal denervation devices and methods.

BACKGROUND OF THE INVENTION

Hypertension is a major public health concern. An estimated 30-40% of the adult population in the developed world suffers from this condition. Diagnosis and treatment of hypertension remain suboptimal. Despite the availability of numerous safe and effective pharmacological therapies, the percentage of patients achieving adequate blood-pressure control to guide-line target values remains low. Much failure of the pharmacological strategy to attain adequate blood-pressure control is attributed to both physician inertia and patient non-compliance and non-adherence to a lifelong pharmacological therapy. Thus, the development of new approaches for the management of hypertension is a priority. These considerations are especially relevant to patients with so-called resistant hypertension (i.e., those unable to achieve target blood-pressure values despite multiple drug therapies at the highest tolerated dose). Such patients are at high risk of major cardiovascular events.

Renal sympathetic efferent and afferent nerves, which lie within and immediately adjacent to the wall of the renal artery, are crucial for initiation and maintenance of systemic hypertension. Indeed, sympathetic nerve modulation as a therapeutic strategy in hypertension had been considered in the past. Surgical methods for thoracic, abdominal, or pelvic sympathetic denervation had been successful in lowering blood pressure in patients with so-called malignant hypertension. However, these methods were associated with high perioperative morbidity and mortality and long-term complications, including bowel, bladder, and erectile dysfunction, in addition to severe postural hypotension. Renal denervation is the application of a chemical agent, or a surgical procedure, or the application of energy to partially or completely damage renal nerves to partially or completely block renal sympathetic nerve activity. Renal denervation reduces or completely blocks renal sympathetic nerve activity, increases renal blood flow, decreases renal plasma norepinephrine content, and reduces the release of renin into the systemic circulation.

The objective of renal denervation is to neutralize the effect of excess renal sympathetic nerve activity which is involved in both arterial hypertension and heart failure. Device-based renal denervation is known in the art. For example, U.S. Patent Application Publication 2011/0118726 titled "Assembly of Staggered Ablation Elements," the contents of which are hereby incorporated by reference herein, describes a catheter based renal denervation device featuring a catheter with an expandable structure connected to the distal end of the catheter. Once the device is located at the desired position within a renal artery or vein, ablation elements connected to the expandable structure can be energized to ablate the desired renal nerves or to otherwise block nerve activity.

Current devices for renal denervation utilize metallic electrodes to apply a radiofrequency ("RF") electrical field to resistively heat the adjacent arterial endothelium. Subsequent heat transfer across the arterial wall, from endothelium to adventitia, results in denervation of the renal nerve. Procedural damage to the renal artery endothelium during a renal denervation process can be undesirable since the subsequent healing response may result in stenosis. Direct exposure of the endothelium to the RF electric field may also result in irreversible electroporation and surface electrolysis. This is because RF fields can have concentrated effects at the tissue surface which are more concentrated than heat transfer to the tissue surface.

Additionally, partial contact of the electrode may expose the circulating blood flow to the concentrated resistive heating zone resulting in coagulation, charring of the electrode surface, and increasing the potential for thrombus formation.

Thus, further improvement of devices and methods for renal denervation would be desirable.

SUMMARY OF THE INVENTION

In one embodiment of the invention, an RF treatment device includes a device body and an assembly connected to the device body. The assembly includes one or more heating elements connected to the device body, each heating element having a conductor and a layer of an RF dissipating material overlying the conductor so that the layer of RF dissipating material is disposed between the conductor and body tissues of a subject when the assembly is in an operative position within the body of the subject.

The RF dissipating material may include a polymeric material, for example one selected from the group consisting of solid polymer electrolytes, polymeric hydrogel electrolytes, polyelectrolytes, ionomers and combinations thereof. The RF dissipating material may alternately include one selected from the group consisting of sulfonated perfluoropolyethers, hydrogenated and fluorinated polyakylene oxides, polyphosphazenes, polyethyleneimines, polyvinyl alcohols, polyvinyl pyrolidones, polyethylene imines, hydrolyzed polyacrylonitrile, crosslinked polypeptides, carboxylate-containing polymers, sulfonic acid-containing polymers, and phosphate-containing polymers.

The polymeric material may further comprise a salt, the salt further comprising a cationic component and an anionic component. The cationic component may be selected from the group consisting of lithium, sodium, potassium and ammonium. The anionic component may be selected from the group consisting of carboxylates, carbonates, phosphates, perchlorates and triflates.

The RF dissipating material may alternately include a ceramic material. The ceramic material may be selected from the group consisting of tricalcium phosphate, hydroxyapatite, carbonates, sulfates, zirconium oxides, zirconium phosphates, lanthanum fluoride, silver sulfide, and Nasicon.

The RF dissipating layer may have a thickness between 10 μm and 100 μm. The RF dissipating layer may have a thickness and a Debye length, the thickness of the polymeric layer being greater than the Debye length. The Debye length may be approximately 1 μm. A ratio of the thickness of the layer of polymeric material to the Debye length of the RF dissipating material may be at least 3:1.

An RF power source may be operatively connected to the at least one heating element. The power source may be capable of providing 6 watts of radiofrequency power at a frequency of 485 KHz.

The device body may include a catheter extending along a longitudinal axis. The heating elements may be distributed around the longitudinal axis.

In another embodiment of the invention, a method of providing RF treatment includes the step of positioning one or more heating elements within a blood vessel of a mammalian subject, each heating element having a conductor and a layer of an RF dissipating material overlying the metallic conductor, the positioning step being performed so that the layer of RF dissipating material is disposed between the conductor and a wall of the blood vessel. The method may also include applying RF power to the conductors of the heating elements to heat tissues of the subject, the RF dissipating material of the heating elements substantially blocking transmission of RF electric fields to the tissues of the subject.

The heating elements may be mounted to an elongated catheter body and the positioning step may include inserting the catheter body into the blood vessel. The blood vessel may be a renal artery and the heating step may be performed so that heat transferred from the heating elements at least partially causes neuromodulation of one or more renal nerves of the subject. The power source may supply about 6 watts of power. The power source may operate at a frequency of about 485 KHz. The at least one heating element may be heated for about 90 seconds.

BRIEF DESCRIPTION OF THE DRAWINGS

FIG. 4A illustrates a side view of a catheter based renal denervation device according to a further embodiment of the invention.

FIG. 4B is a sectional view taken along line 4B-4B in FIG. 4A.

DETAILED DESCRIPTION

Figure 1:
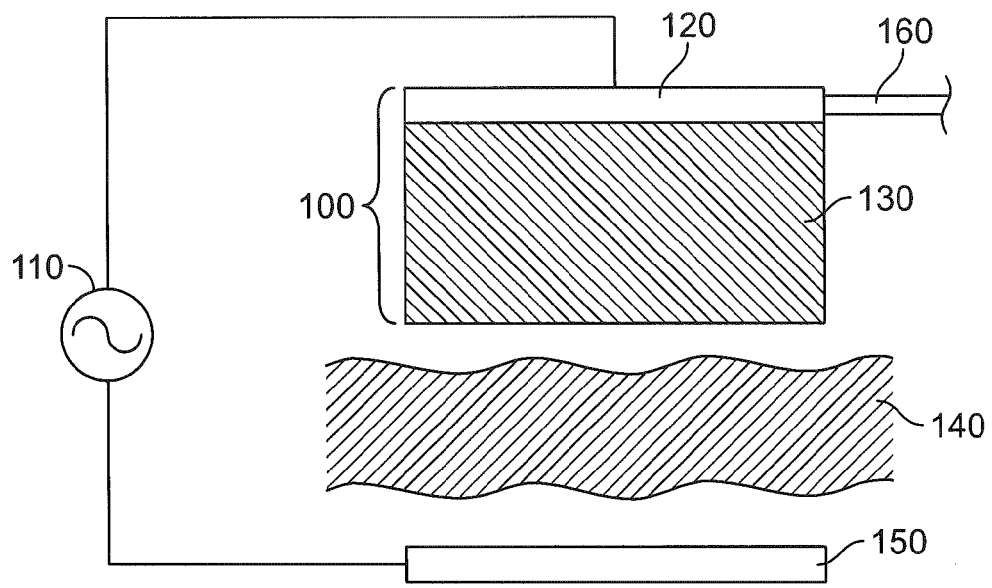
FIG. 1 is a schematic view of one embodiment of a heating element of a treatment device.

A heating element 100 can be used to apply energy during a tissue treatment procedure. In one embodiment of the invention, as shown in FIG. 1, a heating element 100 is brought into proximity with a body tissue 140. The heating element 100 is coupled to a structure 160. Structure 160 may be an ablation catheter as shown in FIGS. 4A-B, configured to introduce the heating element into the body and to the desired treatment area, for example. The heating element 100 is powered with RF alternating current from a source 110. Alternating current is passed to a conductor, for example an electrode 120. The electrode 120 includes a layer of an RF-dissipating material 130. The RF alternating current 110 passing through the electrode 120 heats the layer of RF dissipating material 130 which then transfers heat to tissue 140. The circuit is completed with a dispersive electrode 150, which may, for example, a large grounding pad positioned on the patient's skin, or alternately an adjacent counter-electrode.

The RF dissipating material has properties, such as a high dielectric constant, such that the material is capable of being heated by the RF field. Preferably, the RF dissipating material does not have substantial electronic conductivity arising from free electrons in a conduction band, but may have appreciable ionic conductivity, i.e., electrical conductivity arising from mobile ions in the material. For example, the RF dissipating material may include a polymeric material or a ceramic.

Examples of such polymeric materials include solid polymer electrolyte solutions, polymers having permanent mobile dipole segments, hydrogels and polyelectrolytes.

Solid polymer electrolytes include polymer materials capable of dissolving polar components so as to enable RF heating. These polymers may include, for example, hydrogenated and fluorinated polyalkylene oxides such as polyethylene glycol, polypropylene glycol, and polytetramethylene oxide. Other polymers that can be used as solid polymer electrolytes include, for example, polyphosphazenes and polyethyleneimines.

Hydrogels include hydrophilic polymer networks that absorb significant quantities of water. Hydrogel polymer coatings may, for example, include polyvinyl alcohols, polyvinyl pyrolidones, polyethylene imines, hydrolyzed polyacrylonitrile, water soluble carbohydrates such as hyaluronic acid, and crosslinked polypeptide compounds such as albumin.

Polyelectrolytes include polymers possessing a polar functionality pendant to the polymer chain. Examples of polyelectrolytes can include, for example, carboxylate containing polymers such as polyacrylic acid and sodium salts of polymethacrylic acid, sulfonic acid containing polymers such as perfluorinated polyether sulfonic acids, and phosphate containing compounds such as DNA. Polyelectrolytes can also include polymers having pendant groups possessing large polar moments such as polyphosphorylcholines.

Additional components may be used in combination with a polymer coating, including ionic compositions known to partially or fully dissociate within the polymer matrix. These can include, for example, lithium, potassium, sodium, magnesium and $NR_4^+$ salts of stable anions known to yield high degrees of dissociation. These anions may be, for example, $Cl_4^-$, $CF_3SO_3^-$, $AsF_6^-$, $PF_6^-$, $I^-$, $Br^-$, $SCN^-$, $B_{10}Cl_{10}^-$, $CF_3CO_2^-$, and $Cl^-$.

The polymeric material may be chemically crosslinked to enhance mechanical properties. Alternately the polymeric material may comprise a phase separated block copolymer as a means to impart physical properties similar to a thermoplastic elastomer.

Examples of ceramic dissipating materials include ionically conducting ceramics, including phosphate compositions such as tricalcium phosphate and hydroxyapatite, carbonates, sulfates, and other solid state ceramics known to ionically conduct such as zirconium oxides, zirconium phosphates, lanthanum fluoride, silver sulfide, and Nasicon.

Other additional components can include those with relatively large polar moments and known to dissolve within the polymer matrix. Examples of these may include, for example, high dielectric solvents such as ethylene carbonate, propylene carbonate, butylene carbonate, and cyclic and linear alkyloxylene oligomers.

Combinations of the aforementioned materials also can be used. For example, the combinations can include multiple sub-layers of different RF-dissipating materials cooperatively constituting the layer or can include alloys or mixtures of plural RF-dissipating materials.

In order to reduce or prevent exposure of the tissue 140 to an electric field, the thickness of the layer of polymeric material 130 is preferably significantly larger than the RF field penetration depth (Debye length) within the polymeric material 130. The Debye length refers to the distance from the electrode 120 at which the magnitude of the electric field decreases to 1/e the magnitude of the electric field at the location at which the electrode 120 contacts the layer of polymeric material 130. After a few Debye lengths, the magnitude of the electric field approaches zero asymptotically. The Debye length is dependent, in part, on both the radiofrequency employed and the properties of the polymeric material. The term Debye length, as used herein, refers to the Debye length at the operating frequency of the device. Where the device is connected to an RF power source adapted to supply power at a particular frequency, or accompanied by instructions to connect the device to such a source, the frequency of the source should be taken as the operating frequency of the device. Where the device is associated with instructions to apply a particular frequency, that frequency should be taken as the operating frequency of the device. Absent the aforementioned conditions, the operating frequency of the device should be taken as 1 MHz, which is the highest frequency that would generally be used. In some embodiments of the invention, the Debye length for the frequencies used is on the order of 0.01 µm to 1 µm. The layer of polymeric material 130 is preferably substantially larger than the Debye length, and in some embodiments of the invention can be on the order of 5 µm to 50 µm, more typically 15 µm to 25 µm, for example 20 µm. In one embodiment, the ratio of the length of the polymeric material 130 to the Debye length is 20:1 or more. Other ratios, such as 10:1 or more, 5:1 or more, or 3:1 or more, are also contemplated.

The layer of polymeric material 130 is preferably less electrically conductive than metals. In a preferred embodiment of the invention, the layer of polymeric material 130 is chosen from the group of solid polymer electrolytes, synthetic hydrogels, polyelectrolytes and ionomers. In polymer electrolytes, which are polymers having ionic moieties, conductivity is ionic, not electronic. One example of a polymer electrolyte is sulfonated tetrafluoroethylene, which is also referred to by the trademark NAFION® and is commercially available from the DuPont company of Wilmington, Del.

Figure 2:
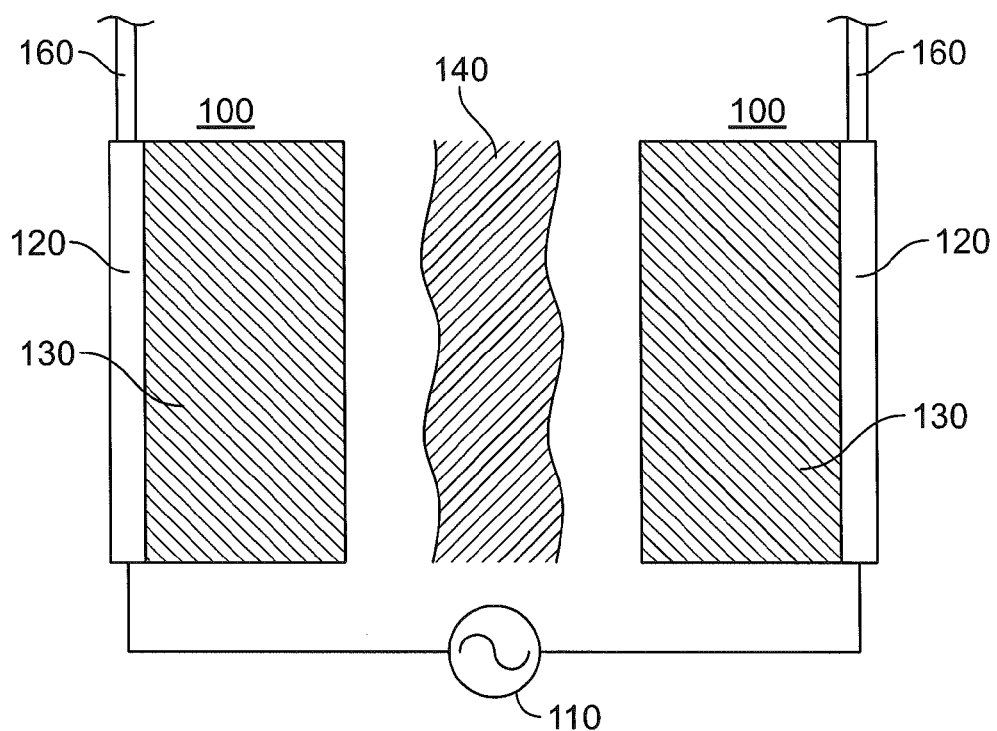
FIG. 2 is a schematic view of an alternate embodiment of a heating element of a treatment device.

Other configurations of heating elements 100 are also contemplated. For example, in a bipolar electrode configuration, a pair or heating elements 100 can be configured to simultaneously contact a tissue 140 when applying energy to the tissue 140, as seen in FIG. 2. In this embodiment, an alternating current power source 110 provides power to two electrodes 120 that flank a tissue 140 that is to be treated in a procedure, such as a renal denervation procedure. Each electrode 120 includes a layer of polymeric material 130 sandwiched between the respective electrodes 120 and the tissue 140 to be treated, and is carried by a structure 160.

Figure 3:
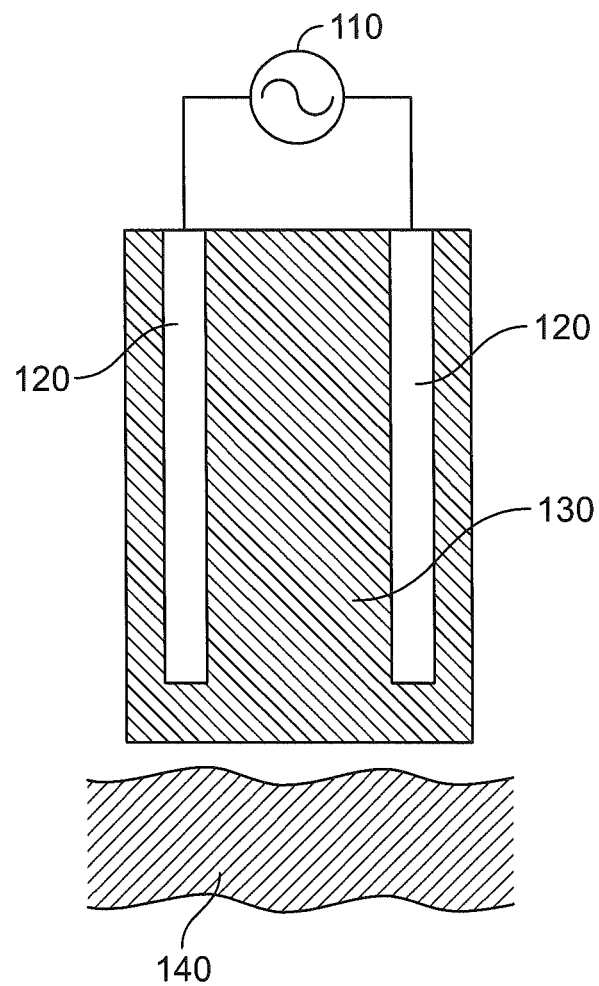
FIG. 3 is a schematic view of still another embodiment of a heating element of a treatment device.

In yet another embodiment of the invention, an alternating current power source 110 provides power to two electrodes 120 encapsulated in a single layer of polymeric material 130, as shown in FIG. 3. The electrodes 120 are carried on a structure (not shown), such as that described below.

Although it is preferable for the polymeric material to fully cover the surface of the electrode that is targeting the tissue, this is not an absolute requirement. For example, minor breaks, holes, openings or other imperfections in the polymeric material will not dramatically affect the dissipation of the electric field between the electrode and the tissue, and also will not dramatically affect the ability of heat to transfer through the polymeric material to the tissue.

An example of a structure 160 that can be used to carry one or more heating elements 100 is illustrated in FIGS. 4A-B. A catheter 10 includes an elongated catheter body 12 extending longitudinally between a proximal end 13 and a distal end 14 along a longitudinal axis 16. An expandable assembly 20, including four struts 30a-d, is connected to the distal end 14 of the catheter body 12. The struts 30a-d are spaced circumferentially about the longitudinal axis 16 of the catheter, as best seen in FIG. 4B, which represents a sectional view of the expandable assembly 20 as viewed along the longitudinal axis 16.

Each strut 30a-d includes a corresponding energy emitter 40a-d, such as an RF electrode 120. The electrodes may include one or more of a number of materials, the materials generally being radiopaque.

The expandable assembly 20 is movable between a collapsed arrangement (not shown) and the expanded arrangement shown in FIG. 4A. A distal end of pull wire 25 is connected to the distal end of the expandable assembly 20 and runs proximally through the catheter body 12 to a location where it can be actuated. Actuating the pull wire 25, for example by the operator grasping and pulling the pull wire 25, causes the expandable assembly 20 to move from a collapsed arrangement (not shown) to the expanded arrangement shown in FIG. 2A. The pull wire 25 is just one of various options that can be used to effectuate movement of an electrode-carrying assembly from a collapsed arrangement to an expanded arrangement. Other mechanisms might include, for example, springs, memory metals, or balloons. A more complete description of suitable structures for the expandable assembly 20, along with various features of struts 30a-d, can be found in U.S. Patent Application Publication 2011/0118726, which is hereby fully incorporated by reference herein.

In use, the catheter 10 with the expandable assembly 20 is inserted into a blood vessel or the like in a collapsed arrangement (inside a guiding sheath or the like) and deployed into the expanded arrangement shown in FIG. 4A. Preferably, the struts 30a-d are designed to allow blood flow in the blood vessel across the expandable assembly 20 and reduce or avoid obstruction. The expandable assembly 20 preferably has no sharp corners or edges but has rounded corners and edges to facilitate easier and smoother movement within the blood vessel. The heating elements in the expanded arrangement contact surfaces to be treated to ablate tissue and/or denervate nerves. The heating elements are positioned on structure 160 so that when the structure is in the operative condition depicted, a portion of the layer 130 of conductive polymer in each heating element (FIG. 1) faces outwardly away from the longitudinal axis. In use, a portion of the polymer layer 130 of each heating element faces the interior wall of the renal artery. The metal electrode 120 (FIG. 1) desirably does not contact the artery wall.

Other structures 160 can be used to carry electrodes to a tissue site for treatment. For example, although FIGS. 4A-B illustrate an assembly with four electrodes, alternate embodiments of a structure could include a single electrode, two electrodes, or any other number of electrodes desired.

Structures other than an expandable basket configuration can also be used in other embodiments of the invention. For example, the electrodes could be connected to an expandable balloon. Another support structure that could be used, by means of example and not limitation, is an assembly with an expandable tree configuration. In such a configuration, one or more resilient biasing members with corresponding electrodes attached thereto are connected to a distal end of a catheter body. During treatment, the biasing members bring the electrodes into proximity with the area of tissue to be treated. Although the devices and methods are described above with reference to renal denervation, they can also be applied in other procedures where tissues must be heated as, for example, thermal ablation procedures.

These and other embodiments of the invention may result in multiple advantages over renal denervation devices in the prior art. For example, embodiments of the invention may (i) eliminate exposure or delivery of the electric field to endothelium; (ii) eliminate direct contact of endothelium with conductive metal and thus preclude Faradaic electrolysis and metal leaching; and (iii) allow for lower operating temperatures for a renal denervation process, minimizing thermal damage to the endothelium, and reducing the possibility of coagulum formation, electrode charring, and thrombotic events, and improve apposition of the electrode to the vessel wall.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An RF treatment device comprising:
 a device body; and
 an assembly connected to the device body comprising one or more heating elements connected to the device body, each heating element having a conductor and a layer of an RF dissipating material overlying the conductor so that the layer of RF dissipating material is disposed between the conductor and body tissues of a subject when the assembly is in an operative position within the body of the subject, wherein the RF dissipating layer has a thickness and a Debye length, the thickness of the dissipating layer being greater than the Debye length.

2. The device of claim 1, wherein the RF dissipating material includes a polymeric material.

3. The device is selected wherein the polymeric from the group consisting of solid polymeric hydrogel electrolytes, polyelectrolytes, ionomers and combinations thereof.

4. The device of claim 2, wherein the polymeric material is selected from the group consisting of sulfonated perfluoropolyethers, hydrogenated and fluorinated polyakylene oxides, polyphosphazenes, polyethyleneimines, polyvinyl alcohols, polyvinyl pyrolidones, hydrolyzed polyacrylonitrile, crosslinked polypeptides, carboxylate-containing polymers, sulfonic acid-containing polymers, and phosphate-containing polymers.

5. The device of claim 4 wherein the polymeric material further comprises a salt, the salt further comprising a cationic component and an anionic component.

6. The device of claim 5 wherein the cationic component is selected from the group consisting of lithium, sodium, potassium and ammonium.

7. The device of claim 5 wherein the anionic component is selected from the group consisting of carboxylates, carbonates, phosphates, perchlorates and triflates.

8. The device of claim 1, wherein the RF dissipating material includes a ceramic material.

9. The device of claim 8, wherein the ceramic material is selected from the group consisting of tricalcium phosphate, hydroxyapatite, carbonates, sulfates, zirconium oxides, zirconium phosphates, lanthanum fluoride, silver sulfide, and Nasicon.

10. The device of claim 1, wherein the RF dissipating layer has a thickness between 10 µm and 100 µm.

11. The device of claim 1, wherein the Debye length is approximately 1 µm.

12. The device of claim 1, wherein a ratio of the thickness of the layer of polymeric material to the Debye length of the RF dissipating material is at least 3:1.

13. The device of claim 1, further comprising an RF power source operatively connected to the at least one heating element.

14. The device of claim 13, wherein the power source is capable of providing 6 watts of radiofrequency power at a frequency of 485 KHz.

15. The device of claim 1, wherein the device body includes a catheter extending along a longitudinal axis.

16. The device of claim 15, wherein the heating elements are distributed around the longitudinal axis.

17. A method of providing RF treatment comprising the steps of:
 positioning one or more heating elements within a blood vessel of a mammalian subject, each heating element having a conductor and a layer of an RF dissipating material overlying the metallic conductor, the positioning step being performed so that the layer of RF dissipating material is disposed between the conductor and a wall of the blood vessel; and
 applying RF power to the conductors of the heating elements to heat tissues of the subject, the RF dissipating material of the heating elements substantially blocking transmission of RF electric fields to the tissues of the subject.

18. A method as claimed in claim 17 wherein the heating elements are mounted to an elongated catheter body and the positioning step includes inserting the catheter body into the blood vessel.

19. A method as claimed in claim 18 wherein the blood vessel is a renal artery and the heating step is performed so that heat transferred from the heating elements at least partially causes neuromodulation of one or more renal nerves of the subject.

20. The method of claim 19, wherein the power source supplies about 6 watts of power.

21. The method of claim 20, wherein the power source operates at a frequency of about 485 KHz.

22. The method of claim 21, wherein the at least one heating element is heated for about 90 seconds.

* * * * *

UNITED STATES PATENT AND TRADEMARK OFFICE
CERTIFICATE OF CORRECTION

PATENT NO. : 9,113,929 B2  
APPLICATION NO. : 13/781136  
DATED : August 25, 2015  
INVENTOR(S) : Parsonage Page 1 of 1

It is certified that error appears in the above-identified patent and that said Letters Patent is hereby corrected as shown below:

In the Specification  
In Column 4, line 38, delete "$Cl_4^-$", and insert therefore -- "$ClO_4^-$ --.

Signed and Sealed this  
Fifteenth Day of March, 2016

Michelle K. Lee  
*Director of the United States Patent and Trademark Office*